US 6,641,303 B2
(12) United States Patent
Yamazaki et al.

(10) Patent No.: US 6,641,303 B2
(45) Date of Patent: Nov. 4, 2003

(54) TEMPERATURE CONTROL SYSTEM FOR HUMIDITY SENSOR

(75) Inventors: Hideharu Yamazaki, Saitama-ken (JP); Tadashi Sato, Saitama-ken (JP); Takashi Haga, Saitama-ken (JP); Yasuyuki Miyahara, Saitama-ken (JP); Masaki Ueno, Saitama-ken (JP); Kei Machida, Saitama-ken (JP)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/231,241

(22) Filed: Aug. 30, 2002

(65) Prior Publication Data

US 2003/0043885 A1 Mar. 6, 2003

(30) Foreign Application Priority Data

Aug. 31, 2001 (JP) ........................................ 2001-263087
Jul. 24, 2002 (JP) ........................................ 2002-214986

(51) Int. Cl.$^7$ .............................................. G01K 13/00
(52) U.S. Cl. ........................... 374/144; 374/16; 374/57; 374/142
(58) Field of Search .............................. 374/16, 50, 57, 374/142, 144, 148, 208

(56) References Cited

U.S. PATENT DOCUMENTS

| | | | | |
|---|---|---|---|---|
| 3,022,668 A | * | 2/1962 | Lawson et al. ............... | 374/115 |
| 4,078,531 A | * | 3/1978 | Hewitt ..................... | 123/198 D |
| 4,203,087 A | * | 5/1980 | Kovac et al. ................ | 338/35 |
| 4,277,742 A | * | 7/1981 | Kovac et al. ................ | 324/689 |
| 4,319,485 A | * | 3/1982 | Terada et al. ............... | 374/142 |
| 6,286,993 B1 | * | 9/2001 | Boll ........................ | 374/144 |
| 6,523,340 B1 | * | 2/2003 | Kurihara et al. ............. | 60/274 |
| 6,581,370 B2 | * | 6/2003 | Ueno et al. ................. | 60/277 |
| 2001/0025484 A1 | * | 10/2001 | Ueno et al. ................. | 60/277 |
| 2002/0011066 A1 | * | 1/2002 | Takakura et al. ............. | 60/277 |
| 2002/0190840 A1 | * | 12/2002 | Fujita et al. ............... | 338/35 |
| 2003/0046979 A1 | * | 3/2003 | Yamazaki et al. ............. | 73/29.02 |
| 2003/0049176 A1 | * | 3/2003 | Sato et al. ................. | 422/83 |
| 2003/0056496 A1 | * | 3/2003 | Ueno et al. ................. | 60/277 |
| 2003/0089100 A1 | * | 5/2003 | Ueno et al. ................. | 60/277 |
| 2003/0106304 A1 | * | 6/2003 | Miyahara et al. ............. | 60/277 |

FOREIGN PATENT DOCUMENTS

| | | | | |
|---|---|---|---|---|
| EP | 0 762 107 A1 | | 3/1997 | |
| JP | 56070449 A | * | 6/1981 | .......... G01N/27/12 |

* cited by examiner

Primary Examiner—Christopher W. Fulton
Assistant Examiner—Lydia M. De Jesús
(74) Attorney, Agent, or Firm—Arent Fox Kintner Plotkin & Kahn, PLLC

(57) ABSTRACT

There is provided a temperature control system for a humidity sensor, which is capable of eliminating impurities attached to a sensor element of the sensor efficiently and sufficiently while preventing the sensor element from being cracked due to heat generated by a heater in a state of condensation formed thereon, and suppressing attachment of impurities to the sensor element, thereby making it possible to preserve an excellent detection accuracy of the humidity sensor. The temperature control system controls the temperature of the sensor element of the humidity sensor arranged in an exhaust pipe for detecting humidity within the exhaust pipe. A heater heats the sensor element. The temperature of the sensor element is detected. When the detected temperature of the sensor element is higher than a predetermined temperature, said heater is operated.

11 Claims, 7 Drawing Sheets

TEMPERATURE CONTROL SYSTEM FOR HUMIDITY SENSOR

BACKGROUND OF THE INVENTION

1. Field of the Invention

This invention relates to a temperature control system for controlling the temperature of a sensor element of a humidity sensor that is arranged in an exhaust pipe of an internal combustion engine for detecting humidity within the exhaust pipe.

2. Description of the Prior Art

There has been proposed an internal combustion engine having an adsorbent arranged in an exhaust system thereof, for adsorbing hydrocarbons in exhaust gases. The adsorbent carries zeolite on its surface. When exhaust gases are passing through the adsorbent, the hydrocarbons contained therein enter small holes of the zeolite, thereby being adsorbed by the adsorbent. The adsorbent of this kind desorbs i.e. releases hydrocarbons once adsorbed thereby when it is heated by exhaust gases to a temperature equal to or higher than a predetermined temperature (e.g. 100 to 250° C.). The desorbed hydrocarbons are recirculated to the engine e.g. via an EGR pipe. The adsorbent repeatedly carries out the adsorption and desorption of hydrocarbons as described above. However, the amount of hydrocarbons which could not be desorbed and permanently remain in the adsorbent may progressively increase or the small holes of the adsorbent may be destroyed by a long-term use thereof. This results in the degradation of the adsorbent to lower an adsorbing capacity of the adsorbent for adsorbing hydrocarbons. This makes it necessary to detect the degree of degradation of the adsorbent.

The present assignee has already proposed a degradation-detecting device for detecting the above degradation of an adsorbent e.g. by Japanese Laid-Open Patent Publication (Kokai) No. 2001-323811. In this degradation-detecting device, attention is paid to proportionality between the adsorbent's capabilities of adsorbing hydrocarbons and of adsorbing moisture, and the humidity of exhaust gases having passed through the adsorbent is detected by the humidity sensor while the adsorbent is adsorbing hydrocarbons, to determine lowering of the adsorbent's capabilities of adsorbing hydrocarbons and moisture, that is, the degradation of the adsorbent, based on the detected humidity. The humidity sensor has a sensor element formed by a porous body having a large number of small holes. When exhaust gases is passing through the sensor element, moisture in the exhaust gases enters the small holes of the porous body, and is adsorbed by the same, based on which the humidity of exhaust gases is detected. As described above, the sensor element is exposed to exhaust gases in detecting humidity of the exhaust gases, and hence water droplets produced by condensation, and impurities, such as unburned components of fuel, contained in the exhaust gases, are attached to the sensor element. In this case, the humidity of the exhaust gases cannot be detected properly, and the degree of degradation of the adsorbent cannot be detected properly, either.

To overcome this problem, in the proposed degradation-detecting device, the temperature of the sensor element is controlled by heating the same by using a heater to eliminate water droplets attached thereto and suppress attachment of water droplets thereto, whereby an excellent detection accuracy of the humidity sensor is maintained. More specifically, in the temperature control of the humidity sensor, the heater is operated for a predetermined time period, judging that condensation has been formed on the sensor element, either when the intake air temperature is lower than a predetermined temperature before the start of the engine, or when idling of the engine has continued for a predetermined time period or longer after the start of the engine.

In the temperature control of the above humidity sensor, the heater is operated for the predetermined time period only under circumstances in which it is presumed that condensation has occurred. However, the above determination of degradation of the adsorbent is carried out while hydrocarbons are being adsorbed by the adsorbent, and hence impurities in exhaust gases other than water droplets may be attached to the humidity sensor. Even if such impurities have been attached, so long as it is not presumed that condensation has been formed, the above temperature control is not carried out, resulting in the degraded detection accuracy of the humidity sensor. Further, since the heater is simply operated for the predetermined time period, there is a fear that the impurities cannot be sufficiently eliminated, e.g. depending on a temperature condition of the exhaust system. Moreover, since the sensor element is suddenly heated by the heater from a state having condensation formed thereon, the temperature of the sensor element sharply rises from a low temperature, which can cause cracking of the sensor element.

SUMMARY OF THE INVENTION

It is an object of the invention to provide a temperature control system for a humidity sensor, which is capable of eliminating impurities attached to a sensor element of the sensor efficiently and sufficiently while preventing the sensor element from being cracked due to heat generated by a heater in a state of condensation formed thereon, and suppressing attachment of impurities to the sensor element, thereby making it possible to preserve an excellent detection accuracy of the humidity sensor.

To attain the above object, the present invention provides a temperature control system for controlling a temperature of a sensor element of a humidity sensor arranged in an exhaust pipe of an internal combustion engine for detecting humidity within the exhaust pipe, the temperature control system comprising:

a heater for heating the sensor element;

temperature-detecting means for detecting the temperature of the sensor element; and heater control means for causing the heater to operate when the temperature of the sensor element detected by the temperature-detecting means is higher than a first predetermined temperature.

According to this temperature control system for a humidity sensor, the heater control means causes the heater to operate when the temperature of the sensor element detected by the temperature-detecting means is higher than a first predetermined temperature, whereby the sensor element is heated. Thus, the heater is operated when the sensor element is in a high temperature condition, so that it is possible to efficiently burn and eliminate impurities attached to the sensor element. This makes it possible to properly restore detection accuracy of the humidity sensor.

Preferably, the first predetermined temperature is a temperature at which condensation cannot be formed on the sensor element.

According to this preferred embodiment, the heater is operated when the temperature of the sensor element is higher than a temperature at which condensation cannot be formed on the sensor element, and hence the sensor element can be heated in a state where no condensation has been formed on the sensor element. Therefore, it is possible to prevent the sensor element from being cracked by heat generated by the heater when it has condensation formed thereon.

Preferably, the heater is configured to generate a variable amount of heat, and the heater control means causes the heater to operate to generate a smaller amount of heat when the temperature of the sensor element is equal to or lower than the first predetermined temperature, than when the temperature of the sensor element is higher than the first predetermined temperature.

According to this preferred embodiment, the heater configured to generate a variable amount of heat is operated to generate a smaller amount of heat when the temperature of the sensor element is equal to or lower than the first predetermined temperature, than when the temperature of the sensor element is higher than the first predetermined temperature. This causes the temperature of the sensor element to slowly rise from a low temperature condition in which condensation has been formed on the sensor element, thereby making it possible to eliminate condensation with minimum power consumption while positively preventing the sensor element from being cracked by a sudden change in temperature.

Preferably, the temperature control system further comprises atmosphere-determining means for determining whether or not an atmosphere in which the humidity sensor is operating is in an oxidizing condition, and the heater control means causes the heater to stop operating when time over which the heater operates with the temperature of the sensor element being higher than a second predetermined temperature high enough to eliminate impurities attached to the sensor element and the atmosphere in which the humidity sensor is operating being in the oxidizing condition has reached a predetermined time period.

According to this preferred embodiment, the heater is stopped from operating when a cumulative time period over which the heater operates with the temperature of the sensor element being high enough to eliminate impurities attached to the sensor element and the atmosphere in which the humidity sensor is operating being in the oxidizing condition has reached a predetermined time period. Thus, the sensor element is heated by the heater for the predetermined time period with the temperature of the sensor element and the atmosphere in which the sensor element is operating being suitable for burning impurities attached to the sensor element. Therefore, it is possible to fully burn and positively eliminate the impurities. Further, since the operation of the heater is stopped when the predetermined time period is reached, it is possible to operate the heater in a just appropriate fashion without excessiveness, and thereby minimize power consumption of the heater.

Preferably, the heater control means causes the heater to operate during stoppage of the engine.

According to this preferred embodiment, the heater is also operated during stoppage of the engine. Therefore, even when the engine has stopped before the impurities have been eliminated by operation of the heater during operation of the engine, it is possible to positively eliminate impurities attached to the sensor element. It should be noted that the stoppage of the engine includes stoppage by an idle stop, i.e. a function of a vehicle for automatically stopping operation of the engine e.g. during waiting at a stoplight. Vehicles having an idle stop feature tend to repeatedly carry out operation and stoppage of their engines at short time intervals, and hence there is a high possibility that the idle stop is executed before completion of elimination of impurities. Therefore, this preferred embodiment makes it possible to efficiently obtain the above-described advantageous effects of the invention.

Preferably, an adsorbent for adsorbing hydrocarbons in exhaust gases is arranged within the intake pipe, and the humidity sensor is arranged in the vicinity of the adsorbent, the humidity sensor being used for determination of degradation of the adsorbent, which is executed based on a result of detection by the humidity sensor after the engine has stopped.

According to this preferred embodiment, the determination of degradation of the adsorbent is carried out after the engine has stopped, i.e. based on the result of detection of the upstream humidity sensor executed in a state in which no exhaust gases are flowing. Thus, the determination of degradation of the adsorbent can be carried out without causing the humidity sensor to be exposed to exhaust gases flowing during operation of the engine. This enables the heater control to be carried out during operation of the engine, so that the temperature of the sensor element can be maintained at a predetermined temperature. This makes it possible to suppress attachment of impurities to the sensor element, whereby an excellent detection accuracy of the humidity sensor can be maintained. Further, since the determination of degradation of the adsorbent can be carried out based on the result of detection by the humidity sensor executed in a condition suppressing attachment of impurities to the sensor element, the determination can be carried out with accuracy.

More preferably, a changeover valve is arranged in the exhaust pipe for switching the exhaust pipe between a main passage and a bypass passage bypassing the main passage, and the humidity sensor is arranged in the bypass passage, the changeover valve being configured to switch the exhaust pipe to the main passage during operation of the engine, except when the hydrocarbons are adsorbed by the adsorbent.

According to this preferred embodiment, in the exhaust pipe, there are provided a main passage and a bypass passage bypassing the main passage, and the exhaust pipe is switched to the main passage during operation of the engine, except when the hydrocarbons are adsorbed by the adsorbent. Thus, during operation of the engine, exhaust gases are caused to flow through the main passage except when the hydrocarbons are absorbed by the adsorbent. This makes it possible to prevent the humidity sensor from being exposed to exhaust gases flowing during operation of the engine. Therefore, it is possible to suppress attachment of impurities to the sensor element.

More preferably, the determination of degradation of the adsorbent is carried out on condition that the engine was operating in a predetermined operating condition before stoppage of the engine.

According to this preferred embodiment, the determination of degradation of the adsorbent is carried out after the engine operating in a predetermined operating condition stopped. In general, the adsorbent desorbs hydrocarbons adsorbed thereby when the temperature thereof becomes equal to or higher than a predetermined temperature. Therefore, by setting the predetermined condition such that the temperature of the adsorbent is high enough to desorb the hydrocarbons, it is possible to carry out the determination of degradation of the adsorbent without being affected by hydrocarbons remaining in the adsorbent. This can increase the accuracy of the determination of degradation of the adsorbent.

Further preferably, the predetermined operating condition of the engine is a condition in which the engine operates with supply of a mixture at or in the vicinity of a stoichiometric air-fuel ratio.

According to this preferred embodiment, the determination of degradation of the adsorbent is carried out after the engine operating with supply of a mixture at or in the vicinity of the stoichiometric air-fuel ratio has stopped. When the air-fuel ratio of the mixture is at or in the vicinity of the stoichiometric air-fuel ratio, the amount of unburned components in exhaust gases is more steady or substantially fixed than when the air-fuel ratio of the mixture is on a richer or leaner side, and hence the determination of degradation of the adsorbent is accurate when it is carried out after the engine has stopped after operating with supply of a mixture at or in the vicinity of the stoichiometric air-fuel ratio. Moreover, when the air-fuel ratio of the mixture is at or in the vicinity of the stoichiometric air-fuel ratio, the amount of moisture in exhaust gases is relatively large with little variation, and hence the atmosphere in which the humidity sensor is operating after the engine operated in such a condition and then stopped is also relatively high in humidity with little variation, which is suitable for the determination of degradation of the adsorbent. Therefore, the degradation determination can be accurately carried out in this state.

The above and other objects, features, and advantages of the invention will become more apparent from the following detailed description taken in conjunction with the accompanying drawings.

DETAILED DESCRIPTION OF A PREFERRED EMBODIMENT

Figure 1:
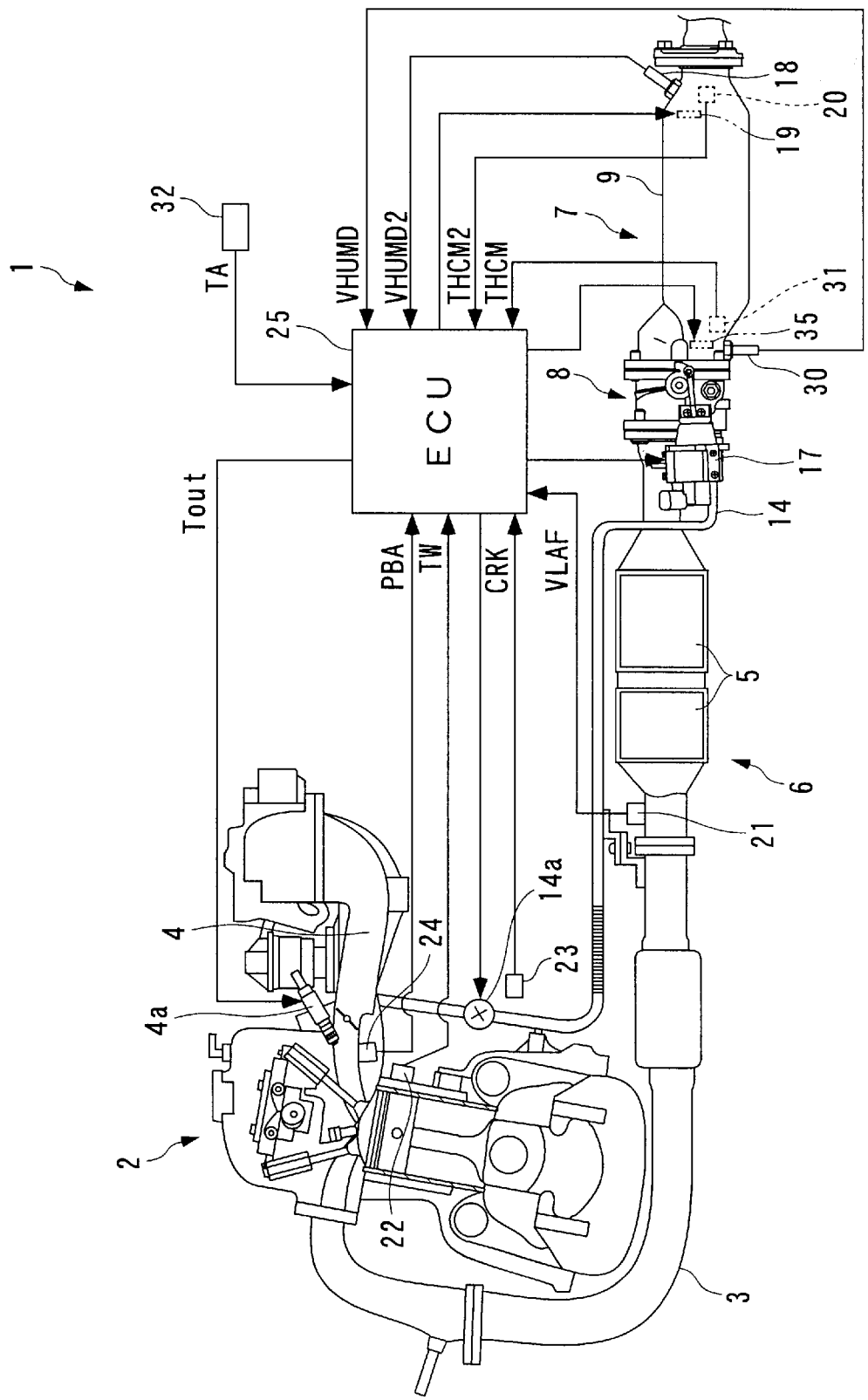
FIG. 1 is a block diagram showing the arrangement of an internal combustion engine to which is applied a temperature control system for a humidity sensor, according to an embodiment of the present invention.

The invention will now be described in detail with reference to the drawings showing a preferred embodiment thereof. Referring first to FIG. 1, there is schematically shown the arrangement of an internal combustion engine 2 (hereinafter simply referred to as "the engine 2") to which is applied a temperature control system 1 for a humidity sensor (hereinafter simply referred to as "the control system 1"), according to the embodiment of the present invention. This engine 2 is e.g. a four-cylinder four-cycle engine installed on a vehicle, not shown, which has an idle stop feature. Further, the engine 2 includes an intake pipe 4 having injectors 4a provided for respective cylinders, and the fuel injection time period Tout of each injector 4a is controlled by an ECU 25, referred to hereinafter.

In an intermediate portion of an exhaust pipe 3 of the engine 2, a catalytic device 6 having a three-way catalyst 5, and a hydrocarbon adsorber 7 for adsorbing hydrocarbons are arranged from the upstream side to the downstream side in the mentioned order as purification devices for purifying exhaust gases. When heated to a temperature equal to or higher than a predetermined temperature (e.g. 300° C.), the three-way catalyst 5 is active and reduces harmful substances (HC, CO and NOx) in exhaust gases passing through the catalytic device 6 by oxidation-reduction catalytic actions thereof.

Figure 2:
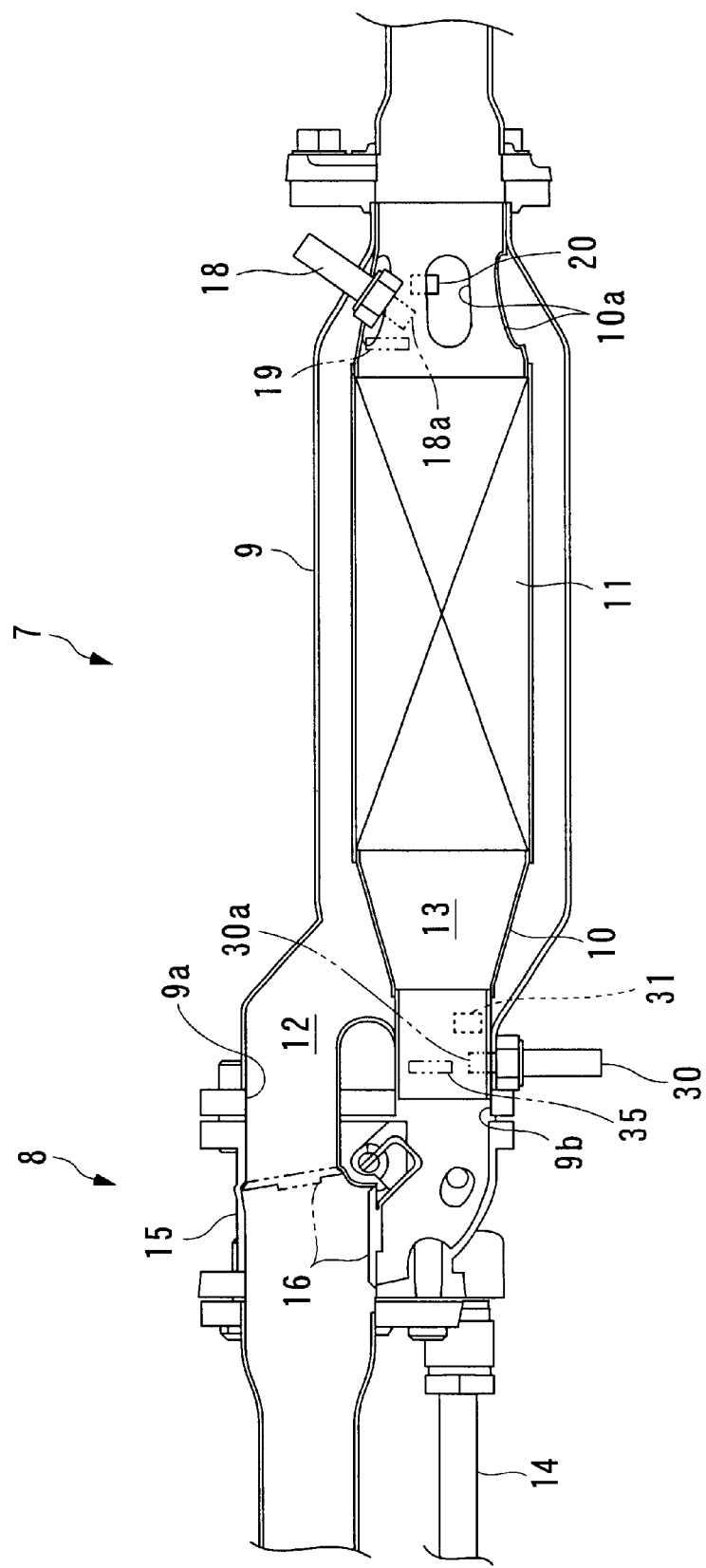
FIG. 2 is an enlarged cross-sectional view of a hydrocarbon adsorber.

The hydrocarbon adsorber 7 adsorbs hydrocarbons in exhaust gases when the engine 2 is in a starting condition (e.g. for about 30 to 40 seconds after the start of the engine) in which the three-way catalyst 5 has not been activated yet, to thereby reduce emission of hydrocarbons from the vehicle. As shown in FIGS. 1 and 2, the hydrocarbon adsorber 7 includes an exhaust passage changeover device 8, a casing 9 forming an outer shell having a generally hollow cylindrical shape, and a cylindrical adsorbent 11 accommodated in the casing 9 for adsorbing hydrocarbons in exhaust gases.

As shown in FIG. 2, the casing 9 has an upstream end thereof bifurcated into upper and lower portions. An upper opening 9a of the upper portion of the upstream end communicates with a space (main passage 12) annular in cross section, formed outside a bypass exhaust pipe 10 in the casing 9, while a lower opening 9b of the lower portion of the upstream end communicates with a space (bypass passage 13) inside the bypass exhaust pipe 10.

The bypass exhaust pipe 10 has an upstream end thereof inserted into the lower opening 9b of the casing 9 and a downstream end thereof inserted into the downstream end portion of the casing 9, in airtight conditions, respectively. Further, the bypass exhaust pipe 10 is formed with a plurality of (five, for instance) communication slots 10a at locations close to the downstream end at circumferentially equal intervals, via which the downstream end portion of the main passage 12 and that of the bypass passage 13, within the casing 11, communicate with each other.

The adsorbent 11 is formed of a metal honeycomb core, not shown, carrying a zeolite on the surface thereof. The zeolite which has high heat resistance adsorbs hydrocarbons when it is in a low temperature condition (e.g. lower than 100° C.) while desorbs i.e. releases the hydrocarbons adsorbed thereby when it is heated to a temperature equal to or higher than a predetermined temperature (e.g. 100 to 250° C.). The desorbed hydrocarbons are recirculated from the hydrocarbon adsorber 7 to the engine 2 via an EGR pipe 14 and the intake pipe 4, for being burned by the engine 2. Further, an EGR control valve 14a is arranged at an intermediate portion of the EGR pipe 14. The ECU 25 controls the EGR control valve 14a to control the operation and stoppage of an EGR (exhaust gas recirculation) system and the amount of EGR.

The exhaust passage changeover device 8 includes a connection pipe 15 having a generally hollow cylindrical shape and connecting the hydrocarbon adsorber 7 configured as above to the catalytic device 6, and a changeover valve 16 which is arranged in the connection pipe 15 for switching the exhaust passage between the main passage 12 and the bypass passage 13. Further, the switching operation of the changeover valve 16 is controlled by a changeover valve actuation control device 17 (see FIG. 1) which is driven by the ECU 25.

In the exhaust passage changeover device 8 configured as above, the changeover valve 16 is normally actuated for pivotal movement to a location indicated by a two-dot chain line in FIG. 2 immediately after the start of the engine 2, whereby the exhaust passage is switched to the bypass passage 13. This allows exhaust gases having passed through the catalytic device 6 to be guided into the bypass passage 13, thereby causing hydrocarbons and moisture in the exhaust gases to be adsorbed by the adsorbent 11. The exhaust gases having passed through the adsorbent 11 further flow downstream so as to be emitted from the vehicle. When a certain time period has elapsed after the start of the engine 2, and the three-way catalyst 5 has been activated, the changeover valve 16 is driven for pivotal movement to a location indicated by a solid line in FIG. 2, whereby the exhaust passage is switched to the main passage 12. This causes exhaust gases having passed through the catalytic device 6 to be guided into the main passage 12 inside the casing 9, flow into the bypass exhaust pipe 10 via the communication slots 10a formed in the downstream end portion of the bypass exhaust pipe 10, and further flow downstream so as to be emitted from the vehicle. Further, when the EGR control valve 14a is opened to start the EGR, part of exhaust gases are recirculated as EGR gases to the intake pipe 4 via the bypass passage 13 and the EGR pipe 14. The hydrocarbons desorbed from the adsorbent 11 are sent to the intake pipe 4, and burned in the engine 2.

Further, a downstream humidity sensor 18 (humidity sensor) is mounted on the casing 9 of the hydrocarbon adsorber 7 at a location downstream of the adsorbent 11 such that it is inserted into the bypass passage 13. The downstream humidity sensor 18 is provided to determine the degree of degradation of the adsorbent 11 during operation of the engine 2, and senses a relative humidity VHUMD2 within the exhaust pipe at a location downstream of the adsorbent 11, and delivers a signal indicative of the sensed relative humidity VHUMD2 to the ECU 25. The downstream humidity sensor 18 has a sensor element 18a which is formed by a porous body made of alumina or the like, and configured to detect the humidity of the exhaust gases based on a resistance value thereof varying with the amount of moisture adsorbed from exhaust gases. Further, the downstream humidity sensor 18 has a heater 19 for heating the sensor element 18a. The heater 19 is configured such that it can generate a variable amount of heat, and the ECU 25 controls the amount of energization of the heater 19 to thereby control the amount of heat generated thereby. The sensor element 18a is provided with a temperature sensor 20 (temperature-detecting means) formed by a thermistor or a platinum resistor. The temperature sensor 20 senses a temperature THCM2 of the sensor element 18a and delivers a signal indicative of the sensed sensor element temperature THCM2 to the ECU 25.

Further, an upstream humidity sensor 30 (humidity sensor) is mounted on the casing 9 at a location upstream of the adsorbent 11 such that it is inserted into the bypass passage 13 for determining the degree of degradation of the adsorbent 11 during stoppage of the engine 2. The upstream humidity sensor 30 is configured similarly to the downstream humidity sensor 18, and senses a relative humidity VHUMD within the exhaust pipe at a location upstream of the adsorbent 11, and delivers a signal indicative of the sensed relative humidity VHUMD to the ECU 25. The upstream humidity sensor 30 and its sensor element 30a has a heater 35 and a temperature sensor 31 (temperature-detecting means) provided therefor, respectively, which are similar to the heater 19 and the temperature sensor 20 described above. The temperature sensor 31 detects a temperature (hereinafter referred to as "sensor element temperature") THCM of the sensor element 30a, and delivers a signal indicative of the detected sensor element temperature THCM to the ECU 25.

Further, an air-fuel ratio sensor of a linear output type (hereinafter referred to as "the LAF sensor") 21 is inserted into the exhaust pipe 3 at a location upstream of the catalytic device 6. The LAF sensor 21 linearly detects an oxygen concentration (air-fuel ratio) of exhaust gases and delivers a signal indicative of the detected oxygen concentration to the ECU 25. The output value VLAF of the LAF sensor 21 is configured to be lower as the air-fuel ratio is richer (i.e. smaller). A coolant temperature sensor 22 formed by a thermistor or the like and a crank angle sensor 23 are attached to the body of the engine 2. The coolant temperature sensor 22 detects a temperature (engine coolant temperature) TW of the engine coolant circulating through the cylinder block of the engine 2 and delivers a signal indicative of the detected engine coolant temperature TW to the ECU 25. The crank angle sensor 23 generates and delivers a pulse of a CRK signal as a pulse signal to the ECU 25 whenever a crankshaft, not shown, of the engine 2 rotates through a predetermined crank angle. The ECU 25 determines the rotational speed of the engine 2 (hereinafter referred to as the "engine rotational speed") NE based on the CRK signal. Inserted into the intake pipe 4 is an intake pressure sensor 24 for detecting the absolute pressure PBA within the intake pipe 4 to deliver a signal indicative of the detected intake pipe absolute pressure PBA to the ECU 25. Further, the ECU 25 is also supplied with a signal indicative of atmospheric air temperature TA from an atmospheric air temperature sensor 32 which detects the atmospheric air temperature TA as an external temperature of the engine 2 and the exhaust pipe 3.

The ECU 25 forms heater control means and atmosphere-determining means of the invention. The ECU 25 is formed by a microcomputer including an I/O interface, a CPU, a RAM, and a ROM, none of which are specifically shown. The signals delivered from the sensors described above to the ECU 25 are each input to the I/O interface for A/D conversion, and then input to the CPU.

The CPU determines an operating condition of the engine 2 based on engine parameter signals received from sensors including those described above, and calculates the fuel injection time period Tout in synchronism with generation of each TDC signal pulse to supply a drive signal based on the calculation to the injector 4a. The CPU operates according to control programs read from the ROM and is responsive to signals from the above sensors, for controlling the adsorbing and desorbing operations of the adsorbent 11 and determining the degree of degradation of the adsorbent 11, as well as carrying out a heater control process for controlling the operations of the heaters 19 and 35 so as to control the respective temperatures of the downstream and upstream humidity sensors 19, 35.

Figure 3:
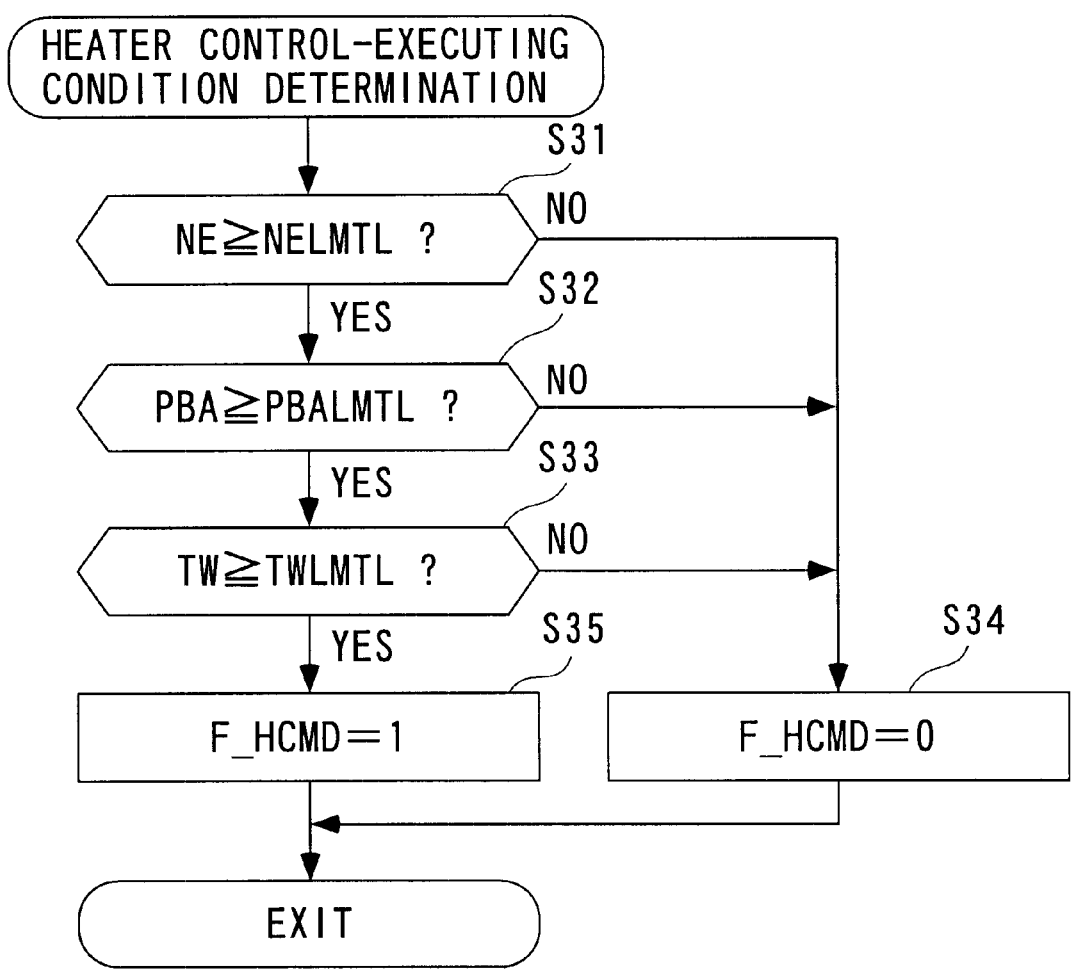
FIG. 3 is a flowchart showing a routine for carrying out a heater control-executing condition-determining process for determining whether or not conditions for executing heater control are satisfied.

The heater control process is carried out in the same manner for both of the downstream and upstream humidity sensors 18, 30. Therefore, the following description of this control will be given as to the upstream humidity sensor 30 alone as a representative of the two sensors. FIG. 3 is a flowchart showing a routine for carrying out a heater control-executing condition-determining process for determining whether or not the heater control should be performed. This process and the heater control process, described in detail hereinafter, are executed at predetermined time intervals (e.g. of 100 msec.). First, in steps S31 to S33, it is determined whether or not the engine rotational speed NE is equal to or higher than a predetermined lower limit value NELMTL (e.g. 650 rpm), whether or not the intake pipe absolute pressure PBA is equal to or higher than a predetermined lower limit value PBALMTL (e.g. 150 mmHg), and whether or not the engine coolant temperature TW is equal to or higher than a predetermined lower limit value TWLMTL (e.g. 80° C.). If any of these answers to these questions is negative (NO), it is judged that the conditions for executing the heater control are not satisfied, so that a heater control-executing condition satisfaction flag F_HCMD is set to 0 in a step S34. On the other hand, if all the answers to the questions of the steps S31 to S33 are affirmative (YES), i.e. if the engine rotational speed NE, the intake pipe absolute pressure PBA, and the engine coolant temperature TW are within the respective predetermined ranges, it is judged that the conditions for executing the heater control are satisfied, and the heater control-executing condition satisfaction flag F_HCMD is set to 1 in a step S35, followed by terminating the program.

Figure 4:
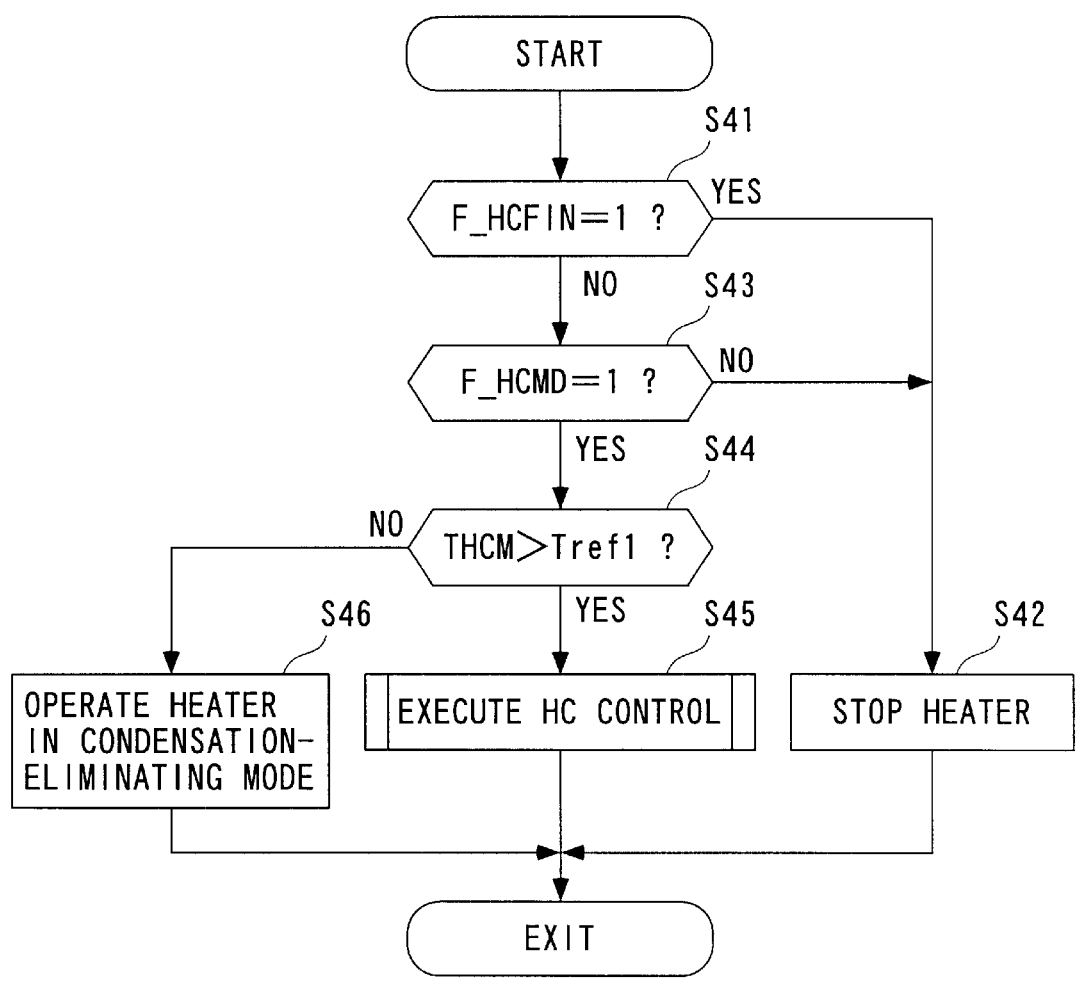
FIG. 4 is a flowchart showing a routine for carrying out a heater control process.

FIG. 4 is a flowchart showing a routine for carrying out the heater control process. First, in a step S41, it is determined whether or not an HC control completion flag F_HCFIN has been set to 1. If F_HCFIN=1 holds, i.e. if heat cleaning control, referred to hereinafter, has been completed, energization of the heater 35 is stopped in a step S42, followed by terminating the program. If the answer to the question of the step S41 is negative (NO), it is determined in a step S43 whether or not the heater control-executing condition satisfaction flag F_HCMD assumes 1. If the answer to the question is negative (NO), i.e. if the conditions for executing the heater control are not satisfied, the program proceeds to the step S42, wherein the energization of the heater 35 is stopped, followed by terminating the program. If the answer to the question of the step S43 is affirmative (YES), it is determined in a step S44 whether or not the sensor element temperature THCM is higher than a first predetermined temperature Tref1. The first predetermined temperature Tref1 is set to a temperature (e.g. 70° C.) at which condensation is not formed on the sensor element 30a. If the answer to the question is affirmative (YES), i.e. if the sensor element temperature THCM is higher than the first predetermined temperature Tref1, the heat cleaning control, referred to hereinafter, is carried out in a step S45, followed by terminating the program. On the other hand, if the answer to the question of the step S44 is negative (NO), i.e. if the sensor element temperature THCM is equal to or lower than the first predetermined temperature Tref1, it is judged that there is a fear that condensation has occurred, and the heater 35 is started in a condensation-eliminating mode in a step S46 to eliminate the condensation, followed by terminating the program. In the condensation-eliminating mode, the heater 35 is operated to generate a smaller amount of heat than when the heat cleaning control is executed.

Figure 5:
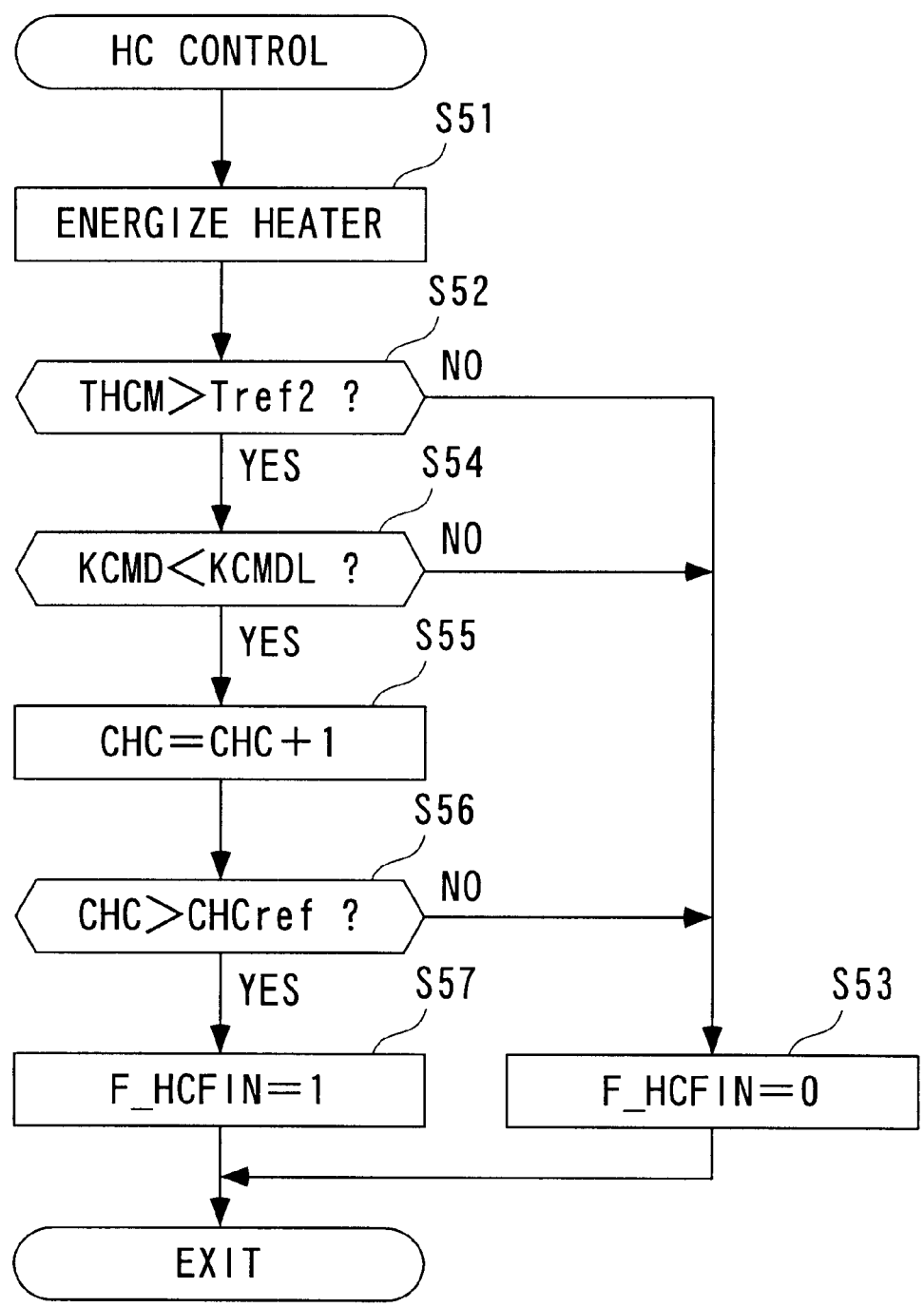
FIG. 5 is a flowchart showing a subroutine for carrying out a heat cleaning control process in a step S45 in FIG. 4.

FIG. 5 is a flowchart showing a subroutine for carrying out a heat cleaning (hereinafter referred to as "HC") control process executed in the step S45 in FIG. 4. The term "heat cleaning (HC)" is intended to mean heating the sensor element 30a by the heater 35 to eliminate impurities attached to the sensor element 30a. First, in a step S51, the heater 35 is energized to heat the sensor element 30a. Then, it is determined in a step S52 whether or not the sensor element temperature THCM is higher than a second predetermined temperature Tref2 higher than the first predetermined temperature Tref1. The second predetermined temperature Tref2 is set to a temperature (e.g. 800° C.) at or above which impurities attached to the sensor element 30a can be burned and eliminated by heat generated by the heater 35.

If the answer to the question of the step S52 is negative (NO), i.e. if the sensor element temperature THCM is equal to or lower than the second predetermined temperature Tref2, the program proceeds to a step S53, wherein the HC control completion flag F_HCFIN is set to 0 to continue the HC control.

If the answer to the question of the step S52 is affirmative (YES), i.e. if the sensor element temperature THCM is higher than the second predetermined temperature Tref2, the program proceeds to a step S54, wherein it is determined whether or not a target air-fuel ratio coefficient KCMD is smaller than a predetermined value KCMDL (e.g. 1.0). The target air-fuel ratio coefficient KCMD is a coefficient set by the ECU 25 according to the engine rotational speed NE, the intake pipe absolute pressure PBA, etc. and used for calculation of the fuel injection time period Tout over which fuel is to be injected into the engine 2. More specifically, when the target air-fuel ratio is equal to a stoichiometric air-fuel ratio, the target air-fuel ratio coefficient KCMD is set to a value of 1.0, and when the target air-fuel ratio is richer than the stoichiometric air-fuel ratio, the target air-fuel ratio coefficient KCMD is set to a value larger than 1.0, whereas when the target air-fuel ratio is leaner than the stoichiometric air-fuel ratio, the target air-fuel ratio coefficient KCMD is set to a value smaller than 1.0.

If the answer to the question of the step S54 is negative (NO), i.e. if KCMD≧KCMDL holds, and hence the air-fuel ratio of the mixture supplied to the engine 2 is controlled to the stoichiometric air-fuel ratio or a richer value so that an atmosphere in which the upstream humidity sensor 30 is operating is not in an oxidizing condition, the program proceeds to the step S53, wherein the HC control completion flag F_HCFIN is set to 0 to continue the HC control.

If the answer to the question of the step S54 is affirmative (YES), i.e. if KCMD<KCMDL holds, and hence if the air-fuel ratio of the mixture supplied to the engine 2 is controlled to a leaner value, including a case where the engine 2 is in a fuel cutoff condition, so that the atmosphere in which the upstream humidity sensor 30 is operating is in the oxidizing condition, the program proceeds to a step S55, wherein the count CHC of a CHC counter is incremented. Then, the program proceeds to a step S56, wherein it is determined whether or not the count CHC of the CHC counter is larger than a predetermined value CHCref (predetermined time period; corresponding to 10 seconds, for instance). If the answer to the question is negative (NO), i.e. if CHC≦CHCref holds, the step S53 is executed to continue the HC control.

If the answer to the question of the step S56 is affirmative (YES), i.e. if time over which the heater 39 has been operating, with the sensor element temperature THCM being higher than the second predetermined temperature Tref2 and the atmosphere in which the upstream humidity sensor 30 is operating being in the oxidizing condition, has reached the predetermined time period corresponding to the predetermined value CHCref, it is judged that impurities attached to the sensor element 30a have been sufficiently burned and eliminated by carrying out the HC control, so that the HC control completion flag F_HCFIN is set to 1 in a step S57 to terminate the HC control, followed by terminating the program. This makes the answer to the question of the step S41 in FIG. 4 affirmative (YES), whereby the energization of the heater 35 is stopped from this time on.

As described above, the HC control is carried out when the sensor element temperature THCM of the upstream humidity sensor 30 is higher than the first predetermined temperature Tref1, whereby the heater 35 is operated to heat the sensor element 30a when condensation has not been formed on the sensor element 30a. Consequently, it is possible to prevent the sensor element 30a from being cracked by heat due to heating of the same by the heater 35 which is executed in a state in which condensation has been formed on the sensor element 30a. Further, the HC control continues to be executed until time over which the heater 39 operates with the sensor element temperature THCM being higher than the second predetermined temperature Tref2 and the atmosphere in which the upstream humidity sensor 30 is operating being in the oxidizing condition reaches the predetermined time period corresponding to the predetermined value CHCref. Therefore, the sensor element 30a can be sufficiently heated by the heater 35 in a state where the sensor element temperature THCM and the atmosphere in which the upstream humidity sensor 30 is operating are suitable for eliminating impurities, such as unburned components of fuel, and cinders and oils of the fuel, attached to the sensor element 30a. Therefore, it is possible to fully burn and thereby positively eliminate the impurities. This makes it possible to properly restore detection accuracy of the upstream humidity sensor 30. Further, by stopping the heater 35 from operating thereafter, it is possible to prevent the heater 35 from operating unnecessarily or excessively, thereby minimizing power consumption.

Further, when the sensor element temperature THCM is lower than the first predetermined temperature Tref1, and hence there is a fear that condensation has been formed, the heater 35 is operated in the condensation-eliminating mode to generate a smaller amount of heat than when the HC control is carried out. This causes the temperature of the sensor element 30a to rise slowly from a low temperature, which enables elimination of the condensation with minimum power consumption while positively preventing the sensor element 30a from being cracked by a sharp change in temperature.

As mentioned hereinabove, the heater control process is also carried out on the downstream humidity sensor 18 in the same manner, whereby the same effects as described above can be obtained for the downstream humidity sensor 18.

Figure 6:
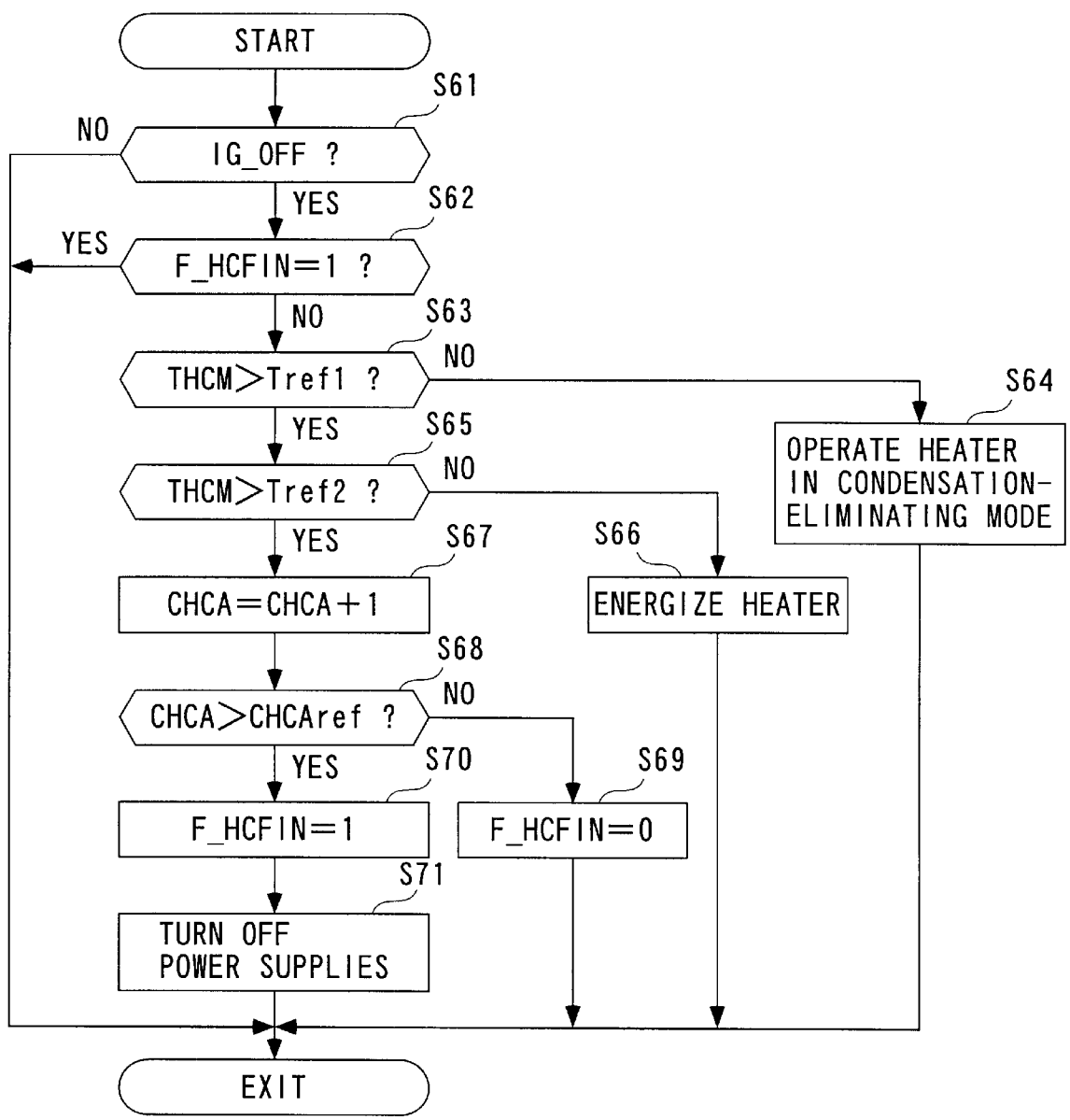
FIG. 6 is a flowchart showing a routine for carrying out a heater control process during stoppage of the engine.

FIG. 6 is a flowchart showing a routine for a heater control process executed during stoppage of the engine 2. First, in a step S61, it is determined whether or not an ignition switch, not shown, of the engine 2 is off or the engine 2 is in an idle stop condition. If the answer to the question is negative (NO), i.e. if the engine 2 is in operation, the program is immediately terminated, whereas if the answer to the question is affirmative (YES), i.e. if the engine is in stoppage, it is determined in a step S62 whether or not the HC control completion flag F__HCFIN assumes 1. If the answer to the question is affirmative (YES), i.e. if the HC control has already been completed, the program is immediately terminated.

If the answer to the question is negative (NO), which means that the HC control has not been completed before stoppage of the engine 2, a control process similar to the heater control process during operation of the engine 2 described above is carried out. First, in a step S63, it is determined whether or not the sensor element temperature THCM is higher than the first predetermined temperature Tref1. If the answer to the question is negative (NO), i.e. if THCM≦Tref1 holds, the program proceeds to a step S64, wherein similarly to the step S46 in FIG. 4, the heater 35 is operated in the condensation-eliminating mode to generate a smaller amount of heat, followed by terminating the program.

If the answer to the question of the step S63 is affirmative (YES), similarly to the step S52 in FIG. 5, it is determined in a step S65 whether or not THCM>Tref2 holds. If the answer to the question is negative (NO), i.e. if the sensor element temperature THCM is equal to or lower than the second predetermined temperature Tref2, the heater 35 is operated in a step S66, followed by terminating the program.

If the answer to the question of the step S65 is affirmative (YES), i.e. if THCM>Tref2 holds, the count CHCA of a CHCA counter is incremented in a step S67, and then it is determined in a step S68 whether or not the count CHCA of the CHCA counter is larger than a value CHCAref (corresponding to 10 seconds, for instance). If the answer to the question is negative (NO), which means that CHCA≧CHCAref holds, the program proceeds to a step S69, wherein the HC control completion flag F__HCFIN is set 0 to continue the HC control.

If the answer to the question of the step S68 is affirmative (YES), i.e. if CHCA>CHCAref holds, the HC control completion flag F__HCFIN is set to 1 in a step S70, and the power supply to the heater 35 and the power supply to the ECU 25 are turned off in a step S71 to terminate the HC control, followed by terminating the program.

As described hereinabove, if the HC control has not been completed during operation of the engine 2, the heater control process continues to be executed even during stoppage of the engine 2 in the same manner as executed during operation of the engine 2. This makes it possible to positively eliminate impurities, and thereby properly restore the detection accuracy of the upstream humidity sensor 30.

Figure 7:
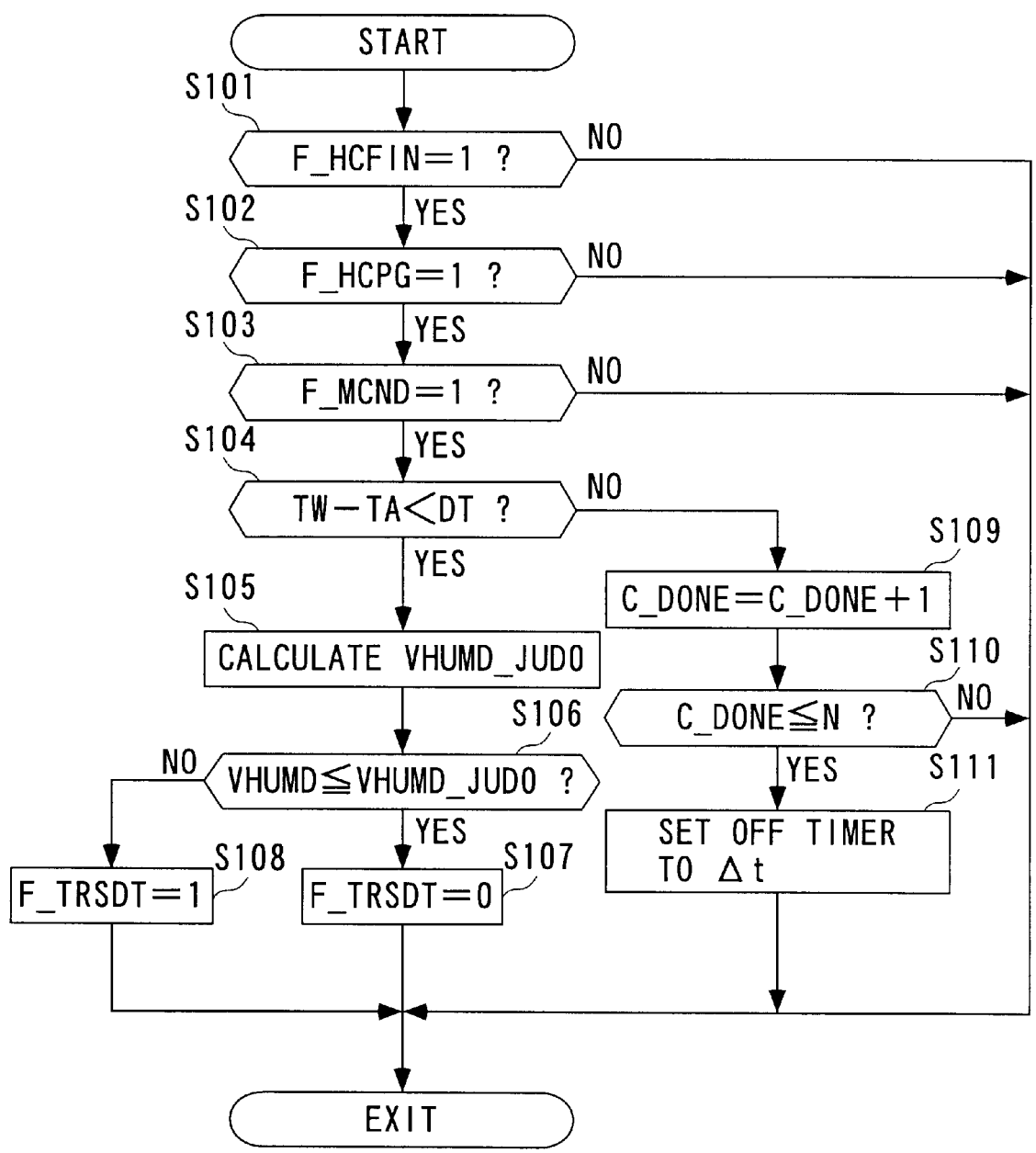
FIG. 7 is a flowchart showing a routine for carrying out a degradation-determining process for determining degradation of an adsorbent after the engine has stopped.

FIG. 7 shows a degradation-determining process for determining degradation of the adsorbent 11, which is carried out after the engine has stopped. This degradation determination is carried out based on the following concept: After the engine 2 has stopped, as the temperature of the adsorbent 11 progressively lowers, the adsorbent 11 adsorbs more moisture, and the adsorption proceeds until the adsorbent 11 is saturated. Therefore, humidity detected in the vicinity of the adsorbent 11 becomes substantially steady or constant. Further, the humidity in this steady state represents a degree of degradation of the adsorbent 11. More specifically, as the degree of degradation of the adsorbent 11 is higher, the adsorbent's capability of adsorbing moisture is lower, and hence when the adsorbent 11 is in the degraded condition, the value of humidity detected in this steady state tends to exhibit a larger value than when the adsorbent 11 is in the normal or non-degraded condition. Therefore, based on the value of the humidity detected in the steady state by the upstream humidity sensor 30, it is possible to determine degradation of the adsorbent 11. Further, since the degradation determination is carried out based on the value of humidity detected when the humidity is in the steady state, it is possible to employ an inexpensive humidity sensor which is relatively low in responsiveness.

The degradation-determining process is started by an off timer, not shown, which starts the ECU 25 again after a predetermined time period (e.g. two hours) has elapsed after the engine stopped to determine the degradation of the adsorbent 11 based on the relative humidity VHUMD detected by the upstream humidity sensor 30. First, in a step S101, it is determined whether or not the HC control completion flag F__HCFIN assumes 1. If the answer to this question is negative (NO), i.e. if the HC control has not been completed during the preceding operation of the engine 2 or during stoppage thereafter, considering that attachment of impurities to the sensor element 30a may prevent the accurate determination of degradation of the adsorbent 11, the degradation determination is not carried out, followed by terminating the present program.

If the answer to the question of the step S101 is affirmative (YES), it is determined in a step S102 whether or not a desorption completion flag F_HCPG assumes 1. If the answer to this question is negative (NO), i.e. if a desorption process for desorbing i.e. releasing adsorbed hydrocarbon was not completed during the preceding operation of the engine 2, there is a fear that the degradation determination of the adsorbent 11 cannot be accurately carried out due to remaining hydrocarbons in the adsorbent 11, and hence the present program is terminated.

If the answer to the question of the step S102 is affirmative (YES), i.e. if the desorption process was completed during the preceding operation of the engine, it is determined whether or not a degradation determination-permitting flag F_MCND assumes 1 (step S103). The degradation determination-permitting flag F_MCND is set to 1, when a state in which the engine coolant temperature TW is higher than a predetermined value (e.g. 85° C.), that is, the temperature of the adsorbent 11 has risen to a value high enough to desorb or release the hydrocarbons adsorbed by the adsorbent 11, and the target air-fuel ratio KCMD is within a predetermined range at or in the vicinity of the stoichiometric air-fuel ratio, has continued for a predetermined time period or longer, judging in such a case that the degradation termination of the adsorbent 11 can be accurately carried out. Therefore, if the answer to the question of the step S103 is negative, i.e. if F_MCND=0 holds, the present program is immediately terminated.

If the answer to the question of the step S103 is affirmative (YES), i.e. if F_MCND=1 holds, it is determined in a step S104 whether or not a value obtained by subtracting the atmospheric air temperature TA from the engine coolant temperature TW is smaller than a predetermined value DT. If the answer to this question is affirmative (YES), i.e. if TW−TA<DT holds, it is judged that the engine coolant temperature TW has dropped to a temperature substantially equal to the atmospheric air temperature, in other words, the temperature of the adsorbent 11 has dropped to the temperature substantially equal to the atmospheric air temperature, and hence the humidity in the vicinity of the adsorbent 11 has become substantially steady. Therefore, by looking up a table, not shown, according to the engine coolant temperature TW, a reference value VHUMD_JUDO with reference to which the degradation of the adsorbent 11 is determined is calculated (step S105). The reference value VHUMD_JUDO is set to a smaller value as the engine coolant temperature TW is lower.

In the following step S106, it is determined whether or not the relative humidity VHUMD is equal to or lower than the reference value VHUMD_JUDO. If the answer to this question is affirmative (YES), i.e. if VHUMD≦VHUMD_JUDO holds, it is judged that the water-adsorbing capability of the adsorbent 11 is high, and hence the adsorbent 11 has not been degraded, so that a degradation flag F_TRSDT is set to 0 to indicate the fact in a step S107, followed by terminating the program.

If the answer to the question of the step S106 is negative (NO), i.e. if VHUMD>VHUMD_JUDO holds, it is judged that the water-adsorbing capability of the adsorbent 11 is low, and hence the adsorbent 11 is degraded, so that the degradation flag F_TRSDT is set to 1 in a step S108, followed by terminating the program.

On the other hand, if the answer to the question of the step S104 is negative (NO), i.e. if TW−TA≧DT holds, in other words, if the temperature of the adsorbent 11 has not dropped to the temperature substantially equal to the atmospheric air temperature, it is judged that the relative humidity VHUMD has not become steady, so that the count C_DONE of a C_DONE counter for counting the number of executions of the degradation determination is incremented in a step S109, and then it is determined in a step S110 whether the count C_DONE is equal to or smaller than an upper limit value N. The count C_DONE of the C_DONE counter is initialized to 0 when the engine 2 is stopped.

If the answer to the question of the step S110 is affirmative (YES), i.e. if C_DONE≦N holds, the time set to the off timer mentioned above is set to a first predetermined time period Δt (e.g. 30 minutes) shorter than the above-mentioned predetermined time period in a step S111, followed by terminating the program. The present process is once interrupted by this, and resumed after the lapse of the first predetermined time period Δt, by the restart of the ECU 25. During this interruption, the count C_DONE is held. Then, in the resumed degradation determination process, when the answer to the question of the step S104 becomes affirmative (YES), the steps S105 et seq. are executed to carry out the degradation determination.

On the other hand, if even in the resumed process, the answer to the question of the step S104 is negative (NO), and at the same time, the answer to the question of the step S110 is negative (NO), i.e. if even with the lapse of a time period corresponding to the upper limit value N in addition to the predetermined time period after the engine 2 stopped, the engine coolant temperature TW has not converged to the atmospheric air temperature TA, it is judged that the degradation of the adsorbent 11 cannot be determined accurately, so that the present program is terminated.

As described above, the degradation determination of the adsorbent 11 is carried out based on the result of detection by the upstream humidity sensor 30 executed after the engine 2 stopped, i.e. in a state in which no exhaust gases are flowing. Further, in the normal operating condition of the engine 2 after the three-way catalyst 5 has been activated, the exhaust passage is switched to the main passage 12, and the exhaust gases do not flow toward the upstream humidity sensor 30. Thus, the upstream humidity sensor 30 is prevented from being exposed to exhaust gases flowing during operation of the engine 2, except a time period during which hydrocarbons are adsorbed at or immediately after a cold start of the engine 2, and the heater control can be carried out during operation of the engine 2, whereby the sensor element temperature THCM can be maintained at a predetermined temperature. Therefore, it is possible to prevent impurities from being attached to the sensor element 30a, and hence preserve an excellent detection accuracy of the upstream humidity sensor 30.

Further, the degradation determination of the adsorbent 11 is carried out while suppressing attachment of impurities thereto, and also on condition that the HC control has been completed, i.e. after eliminating impurities attached to the sensor element 30a. Further, the degradation determination is carried out on condition that the engine 2 was operating with supply of the mixture at or in the vicinity of the stoichiometric air-fuel ratio, i.e. in a condition suitable for the degradation determination in which the humidity of an atmosphere in which the upstream humidity sensor 30 is operating is relatively high with little variation. This condition combined with preservation of the excellent detection accuracy of the upstream humidity sensor 30 makes it possible to carry out accurate degradation determination of the adsorbent.

It should be noted that the invention is not limited to the embodiment described above, but it can be practiced in various ways. For instance, although in the above embodiment, the sensor element temperature THCM is detected by using the temperature sensors 20, 30, it may be estimated by arithmetic operations based on operating conditions of the engine 2. Further, although determination of whether or not the atmosphere in which the upstream humidity sensor 30 is operating is in the oxidizing condition is carried out based on the target air-fuel ratio coefficient KCMD, this is not limitative but this determination may be carried out based on the concentration of oxygen within exhaust gases, detected by the LAF sensor 21. Further, in place of the adsorbent 11 of the embodiment, there may be used a hydrocarbon adsorbing catalyst of a hybrid type in which an adsorbent and a three-way catalyst are provided in combination. This hydrocarbon-absorbing catalyst adsorbs hydrocarbons in a state in which the catalyst has not been activated at a cold start of the engine 2, and then, after activation of the catalyst, the exhaust gases are purified by oxidation-reduction catalytic action thereof. Therefore, even with the use of the hydrocarbon-adsorbing catalyst, the same advantageous effects as provided by the above embodiment can be obtained.

It is further understood by those skilled in the art that the foregoing is a preferred embodiment of the invention, and that various changes and modifications may be made without departing from the spirit and scope thereof.

What is claimed is:

1. A temperature control system for controlling a temperature of a sensor element of a humidity sensor arranged in an exhaust pipe of an internal combustion engine for detecting humidity within the exhaust pipe, the temperature control system comprising:
   a heater for heating the sensor element;
   temperature-detecting means for detecting the temperature of the sensor element; and
   heater control means for causing said heater to operate when the temperature of the sensor element detected by said temperature-detecting means is higher than a first predetermined temperature.

2. A temperature control system according to claim 1, wherein the first predetermined temperature is a temperature at which condensation cannot be formed on the sensor element.

3. A temperature control system according to claim 1, wherein said heater is configured to generate a variable amount of heat, and
   wherein said heater control means causes said heater to operate to generate a smaller amount of heat when the temperature of the sensor element is equal to or lower than the first predetermined temperature, than when the temperature of the sensor element is higher than the first predetermined temperature.

4. A temperature control system according to claim 1, further comprising atmosphere-determining means for determining whether or not an atmosphere in which the humidity sensor is operating is in an oxidizing condition, and
   wherein said heater control means causes said heater to stop operating when time over which said heater operates with the temperature of the sensor element being higher than a second predetermined temperature high enough to eliminate impurities attached to the sensor element and the atmosphere in which the humidity sensor is operating being in the oxidizing condition has reached a predetermined time period.

5. A temperature control system according to claim 1, wherein said heater control means causes said heater to operate during stoppage of the engine.

6. A temperature control system according to claim 1, wherein an adsorbent for adsorbing hydrocarbons in exhaust gases is arranged within the intake pipe, and
   wherein the humidity sensor is arranged in the vicinity of the adsorbent, and
   wherein the humidity sensor is used for determination of degradation of the adsorbent, which is executed based on a result of detection by the humidity sensor after the engine has stopped.

7. A temperature control system according to claim 6, wherein a changeover valve is arranged in the exhaust pipe for switching the exhaust pipe between a main passage and a bypass passage bypassing the main passage, and
   wherein the humidity sensor is arranged in the bypass passage, and
   wherein the changeover valve is configured to switch the exhaust pipe to the main passage during operation of the engine, except when the hydrocarbons are adsorbed by the adsorbent.

8. A temperature control system according to claim 7, wherein the determination of degradation of the adsorbent is carried out on condition that the engine was operating in a predetermined operating condition before stoppage of the engine.

9. A temperature control system according to claim 8, wherein the predetermined operating condition of the engine is a condition in which the engine operates with supply of a mixture at or in the vicinity of a stoichiometric air-fuel ratio.

10. A temperature control system according to claim 6, wherein the determination of degradation of the adsorbent is carried out on condition that the engine was operating in a predetermined operating condition before stoppage of the engine.

11. A temperature control system according to claim 10, wherein the predetermined operating condition of the engine is a condition in which the engine operates with supply of a mixture at or in the vicinity of a stoichiometric air-fuel ratio.

* * * * *